United States Patent
McGrath et al.

(10) Patent No.: US 6,761,810 B2
(45) Date of Patent: Jul. 13, 2004

(54) AUTOMATED APPARATUS INCLUDING A ROBOTIC ARM FOR LOADING SAMPLES INTO WELLS FOR FIRST DIMENSION ELECTROPHORESIS SEPARATION

(75) Inventors: Andrew McGrath, Burtonsville, MD (US); N. Leigh Anderson, Washington, DC (US); Jack Goodman, Lusby, MD (US)

(73) Assignee: Large Scale Proteomics Corp., Vacaville, CA (US)

( * ) Notice: Subject to any disclaimer, the term of this patent is extended or adjusted under 35 U.S.C. 154(b) by 468 days.

(21) Appl. No.: 09/801,831

(22) Filed: Mar. 9, 2001

(65) Prior Publication Data

US 2002/0008033 A1 Jan. 24, 2002

Related U.S. Application Data

(63) Continuation-in-part of application No. 09/621,484, filed on Jul. 21, 2000, now Pat. No. 6,537,434.

(51) Int. Cl.⁷ ..................... G01N 27/26; G01N 27/447; G01N 35/00; G01N 35/10
(52) U.S. Cl. ..................... 204/459; 204/456; 204/465; 204/606; 204/615; 204/610; 422/63; 422/64; 422/65; 422/67; 436/43
(58) Field of Search .................. 204/459, 456, 204/465, 606, 610, 615; 422/63, 64, 65, 67; 436/43

(56) References Cited

U.S. PATENT DOCUMENTS

| | | | | |
|---|---|---|---|---|
| 4,048,049 | A | | 9/1977 | Hoefer .................. 204/606 |
| 4,284,491 | A | | 8/1981 | Vesterberg ............. 204/606 |
| 4,909,920 | A | * | 3/1990 | Sarrine et al. .......... 204/457 |
| 5,356,525 | A | * | 10/1994 | Goodale et al. ......... 204/602 |
| 5,993,627 | A | | 11/1999 | Anderson et al. ....... 204/456 |
| 6,537,434 | B1 | * | 3/2003 | McGrath et al. ........ 204/459 |
| 6,554,991 | B1 | * | 4/2003 | Goodman et al. ...... 204/613 |
| 6,652,724 | B2 | * | 11/2003 | Michael et al. ......... 204/613 |
| 2001/0027920 | A1 | * | 10/2001 | Anderson et al. ....... 204/462 |
| 2002/0025278 | A1 | * | 2/2002 | Anderson et al. ........ 422/99 |
| 2002/0027078 | A1 | * | 3/2002 | Anderson et al. ....... 204/618 |
| 2002/0108857 | A1 | * | 8/2002 | Paschetto et al. ....... 204/457 |
| 2002/0146832 | A1 | * | 10/2002 | Michel et al. ............ 436/43 |
| 2002/0151076 | A1 | * | 10/2002 | Anderson et al. ........ 436/43 |

* cited by examiner

*Primary Examiner*—Alan Diamond
(74) *Attorney, Agent, or Firm*—John C. Robbins; John E. Tarcza

(57) ABSTRACT

An automated assembly for performing first dimension electrophoresis is described herein that includes a supply magazine, an electrophoresis tank and an automated transferring device that robotically transfers biological samples from sample vials retained in the supply magazine, and delivers the biological samples one by one to tube gels supported in a rack within the electrophoresis tank. The transferring device is configured to move in three dimensions with respect to the supply magazine and the rack for flexible sample delivery.

45 Claims, 11 Drawing Sheets

AUTOMATED APPARATUS INCLUDING A ROBOTIC ARM FOR LOADING SAMPLES INTO WELLS FOR FIRST DIMENSION ELECTROPHORESIS SEPARATION

CROSS-REFERENCE TO RELATED APPLICATION

This application is a Continuation-In-Part application of U.S. application Ser. No. 09/621,484 filed Jul. 21, 2000 now U.S. Pat. No. 6,537,434 for First Dimension Electrophoresis Separation Method and Apparatus, which hereby incorporated by reference in its entirety.

FIELD OF THE INVENTION

The present invention is directed to a method and automated apparatus for performing isoelectric focusing of macromolecules, and particularly proteins. More particularly, the present invention is directed to an automated apparatus for supplying protein samples from a sample well to a gel tube for the first dimension isoelectric focusing of the protein sample.

BACKGROUND OF THE INVENTION

Isoelectric focusing (IEF) is an electrophoretic technique for the analysis, separation and purification of various biological materials. Since many of the complex molecules of biological interest are amphoteric in nature, they are typically amenable to IEF separation.

Isoelectric separation is a known process that has been used for many years. An isoelectric focusing gel, such as an acrylamide gel, is placed or polymerized in a tube having open ends. Each open end is positioned in a bath containing a buffer solution. One buffer solution is typically a sodium hydroxide solution to contact one end of the gel tube. The other buffer solution is typically a phosphoric acid solution at the opposite end of the tube to produce a pH gradient between the two ends of the tube. When current is applied, the two buffer solutions, together with ampholytes incorporated into the gel composition or titratable gel monomers incorporated into the gel, provide an electric potential through the gel along the length of the tube. The sample to be analyzed is applied to a top end of the gel in a tube and an electric current is applied to an electrode in each of the buffer solutions. The molecules in the sample migrate through the gel under the influence of the electric potential until they reach their isoelectric point.

The separation of macromolecules, and particularly proteins, often is carried out by a two-dimensional electrophoresis separation process. The two-dimensional electrophoresis separation typically involves the sequential separation by isoelectric focusing of a sample in a gel tube followed by slab gel electrophoresis. The isoelectric focusing process is often referred to as first dimension separation. Slab gel electrophoresis, often referred to as second dimension separation, utilizes an electrophoresis gel molded between two glass plates. A gel strip or cylinder in which the protein sample has been resolved by the first dimension isoelectric focusing is placed along one edge of the slab gel. The opposite ends of the gel slab are immersed in a buffer solution and an electric current is applied between the ends to provide an electric potential through the gel slab. The proteins are then allowed to migrate through the gel slab under an applied voltage.

Charged detergents, such as sodium dodecyl sulfate, contained in the slab gel bind to the protein molecules. The detergents tend to unfold the protein molecules into rods having a length proportional to the length of the polypeptide chain and thus proportional to the molecular weight of the polypeptide. A protein complexed with a charged detergent is highly charged, which causes the protein-detergent complex to move in an applied electric field. When the slab gel, such as a polyacrylamide gel, functions as a sieve, the movement of the longer and higher molecular weight molecules is retarded compared to the shorter, lower molecular weight molecules.

Electrophoresis separation is generally labor intensive since numerous samples are run simultaneously. In the first dimension separation, the gel tubes are prepared and placed in a suitable tank of buffer solutions. The protein samples are then manually placed on the end of a gel tube. When hundreds of protein samples are prepared daily for isoelectric focusing, the manual steps significantly increase the time requirements for performing the first dimension separation. Accordingly, there is a need in the industry for improved methods and devices for conducting first dimension isoelectric focusing.

SUMMARY OF THE INVENTION

The present invention is directed to a method and apparatus for the electrophoresis separation of macromolecules and particularly proteins. More particularly, the invention is directed to an automated apparatus for first dimensional isoelectric focusing of proteins and other macromolecules.

Accordingly, a primary aspect of the invention is to provide an automated apparatus for handling and manipulating a large number of samples for electrophoresis separation.

Another aspect of the invention is to provide an automated apparatus for sequentially transferring a large number of biological samples from a respective sample container to a respective gel tube for performing electrophoresis separation of the sample.

A further aspect of the invention is to provide an automated apparatus for transferring a biological sample from a sample container to a gel tube where information identifying the sample and the location of the sample is stored in a computer.

Another aspect of the invention is to provide an automated apparatus for electrophoresis separation including a sample container magazine having a holding device for holding a sample container stationary while a sample is being removed.

A further aspect of the invention is to provide an automated apparatus for electrophoresis separation including a computer controlled arm having a pipette for piercing a septum in a sample container and removing a selected quantity of a sample from the container.

Still another aspect of the invention is to provide an automated apparatus for electrophoresis separation including a computer controlled arm having a pipette, and a sample container holding device for holding the sample container stationary while the pipette penetrates and is withdrawn from a septum in the sample container.

Another aspect of the invention is to provide an automated apparatus for transferring a plurality of biological samples to a respective gel tube where the assembly has a computer for recording and tracking the location of the samples.

A further aspect of the invention is to provide an automated apparatus for transferring a plurality of samples to a respective gel tube, wherein the apparatus includes a support member, a movable arm coupled to the support member and is movable along a longitudinal dimension of the support member, and a pipette mounted on the movable arm that is movable vertically for withdrawing a sample from a container and for dispensing a sample to a gel tube.

Another aspect of the invention is to provide an automated apparatus for electrophoresis separation having a robotic arm with a pipette that is movable in three dimensions and where the pipette is movable from a sample withdrawing position to a sample dispensing position.

A further aspect of the invention is to provide an automated apparatus for electrophoresis separation of macromolecules, where the apparatus has a plurality of electrophoresis gel tanks, each supporting a parallel row of gel tubes. The apparatus has a movable robotic arm that is able to transfer a sample from a sample vessel to a selected gel tube.

Another aspect of the invention is to provide a rack for supporting a plurality of gel tubes in an electrophoresis tank and where the rack has an open well containing a buffer solution for electrophoresis separation and a guide for guiding a pipette to an end of a gel tube that is positioned in the bottom of the well.

Still another aspect of the invention is to provide an automated transferring device for transferring samples from a sample container to a gel tube where the device includes a stationary cover member positioned above an electrophoresis tank and where the cover member includes a plurality of apertures aligned with the gel tubes.

A further aspect of the invention is to provide an automated transferring device for transferring samples from a container to an electrophoresis device where the transferring device includes a cover member having a plurality of apertures aligned in spaced apart rows and aligned with the electrophoresis device.

Another aspect of the invention is to provide an electrophoresis separation apparatus having a computer for controlling an electric power supply to the gel tanks and for the acquisition of run data for quality control.

The foregoing aspects and advantages of the invention are basically attained by providing an automated first dimensional electrophoresis separation apparatus comprising an electrophoresis assembly supporting a plurality of gel tubes containing an electrophoretic gel. Each of the tubes has a first open end and second open end and a supply magazine for containing a plurality of sample containers. Each sample container contains a sample to be subjected to electrophoresis. A transferring device is provided for sequentially removing a sample from a preselected sample container and transferring the sample to a first end of a respective gel tube. The transferring device includes a pipette that is movable in three dimensions between the supply magazine and a gel tube of the electrophoresis assembly. A microprocessor is operatively connected to the transferring device to automatically control the transfer of the sample to the respective gel tubes.

The aspects of the invention are further attained by providing an automated first dimension electrophoresis separation assembly comprising an electrophoresis assembly including at least one tank and a plurality of gel tubes vertically supported in the tank and arranged in a row. The gel tubes have an open top end. A supply magazine is provided for containing a plurality of sample containers. Each of the sample containers contains a liquid sample. A movable arm is movable in a substantially linear horizontal first direction between the supply magazine and the electrophoresis assembly. A movable pipette is coupled to the arm and is movable along a longitudinal dimension of the movable arm in a horizontal second direction substantially perpendicular to the first direction. The pipette is further movable in a vertical direction with respect to the movable arm. The pipette is movable from a first position for removing a sample from a sample container to a second position for dispensing a sample in a respective gel tube.

The aspects of the invention are still further attained by providing an apparatus for loading a biological sample in to an electrophoresis device. The apparatus comprises a base, a vertical support, and a stationary cover member spaced from the base. The cover has a top surface, a bottom surface and a plurality of apertures extending between the top and bottom surfaces and arranged in a plurality of spaced apart rows. The bottom surface of the cover member is positioned to receive a plurality of electrophoresis devices. The apparatus also includes a supply magazine for containing a plurality of sample containers that contain a biological sample. A robotic arm is movable between the supply magazine and a selected aperture of the cover member. The robotic arm has a pipette for withdrawing a sample from a sample container and delivering the sample through the aperture in the cover member to the electrophoresis device below the cover member. A microprocessor is operatively connected to the robotic arm for operating the robotic arm and the pipette.

The aspects, advantages and salient features of the invention will become apparent to one skilled in the art in view of the following detailed description of the invention in conjunction with the annexed drawings which form a part of this original disclosure.

BRIEF DESCRIPTION OF THE DRAWINGS

The following is a brief description of the drawings, in which.

DETAILED DESCRIPTION OF THE INVENTION

Figure 1:
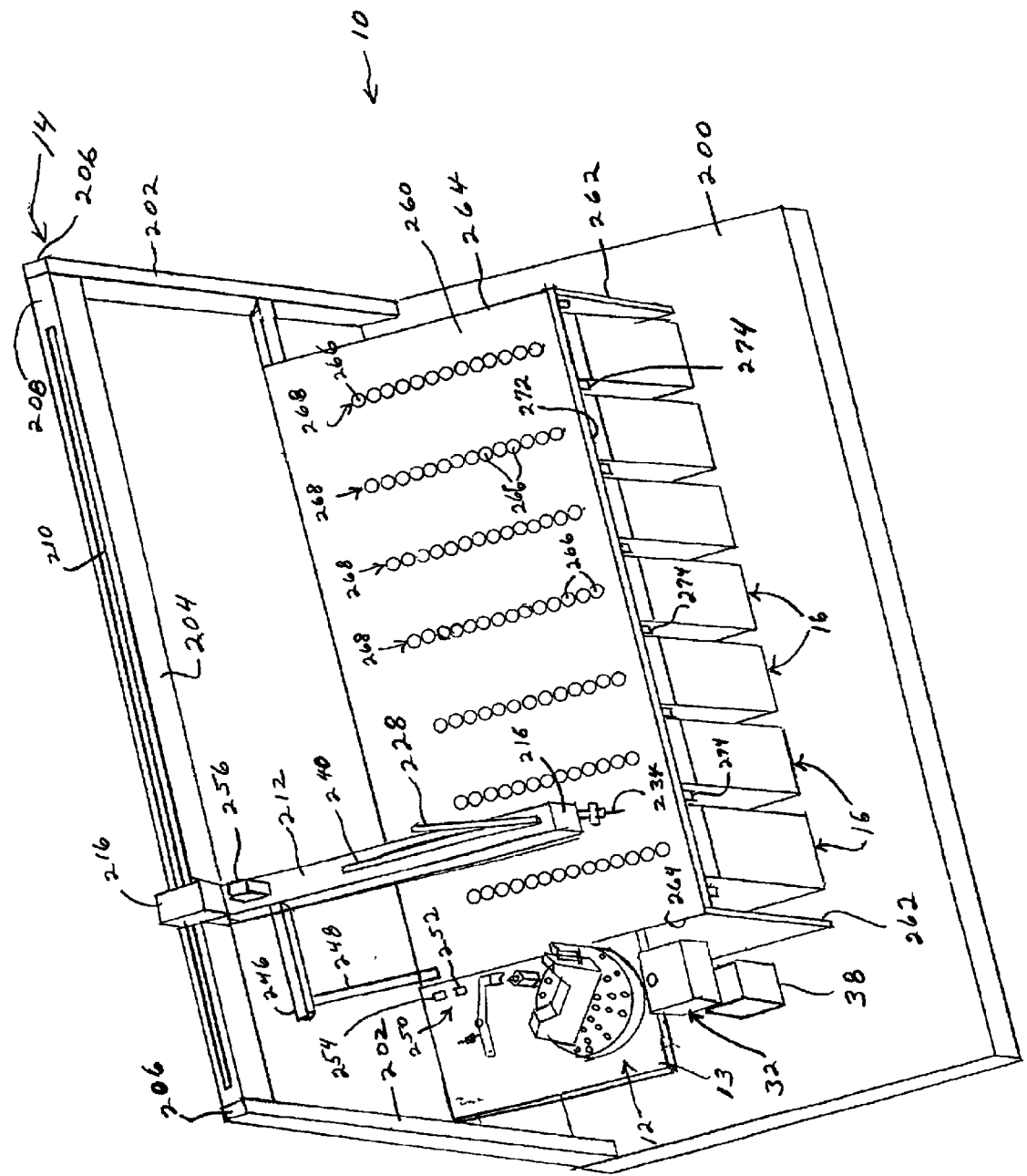
FIG. 1 is a perspective view of the apparatus of the invention showing the electrophoresis gel tanks, sample supply magazine and transferring device for transferring a sample from a sample container to a selected gel tube in a gel tank.

The present invention is directed to a method and apparatus for performing first dimension electrophoresis separation of a biological sample. In particular, the invention is directed to an automated apparatus for loading a plurality of samples into a respective tube containing an isoelectric gel and simultaneously performing electrophoresis separation of the samples.

The method and apparatus of the invention are used primarily in sequence with a second dimension electrophoresis separation step for isolating and recovering specific proteins in a sample. As discussed hereinafter in greater detail, the first dimension separation utilizes an electrophoresis gel in a tube having each end placed in contact with a buffer solution. An electric potential is applied across the ends of the gel tube to cause the proteins to migrate through the gel. The electrophoresis gel, such as IPG gels, and the buffer solutions are standard materials as known in the art of electrophoresis.

The biological samples to be subjected to the electrophoresis separation are typically protein samples. The protein samples are usually solubilized in an aqueous, denaturing solution such as 9 M urea, 2% NP-40 (a non-ionic detergent), 2% of a pH 8–10.5 ampholyte mixture and 1% dithiothreitol (DTT). The urea and NP-40 dissociate complexes of proteins with other proteins and with DNA and RNA. The ampholyte mixture establishes a high pH outside the range where most proteolytic enzymes are active and prevent modification of the sample protein by the ampholyte. The ampholyte further complexes with DNA present in the nuclei of sample cells and allows DNA-binding proteins to be released while preventing the DNA from swelling into a viscous gel that interferes with IEF separation. The dithiothreitol reduces the disulfide bonds in the proteins and allows them to unfold and assume an open structure that is more amenable for separation. Tissue samples are often solubilized by homogenizing in a solubilizing solution. The resulting mixture is centrifuged to remove insoluble material.

The method and apparatus of the invention are used in the first dimension separation of a two-dimensional separation system. The first dimension separation uses an isoelectric focusing gel, such as an acrylamide gel with a catalyst, focusing compounds and cross-linking agents. The gel is placed in a tube, such as a glass tube, having open ends. The bottom end of the tube is placed in a $H_3PO_4$ buffer solution and the top end placed in a sodium hydroxide buffer solution to establish a pH gradient along the gel. The sample material is applied to the top end of the tube and allowed to migrate through the gel under the influence of an electrical potential. Generally, an electric current of about 1200 volts is applied between the upper and lower buffer solutions for about 20 hours. The isoelectric focusing gel and buffer solutions are conventional materials known in the art for first dimension separation.

Referring to the drawings, the electrophoresis apparatus 10 includes a sample supply magazine 12, an automated robotic transferring assembly 14 and a plurality of electrophoresis tanks 16. Tanks 16 contain several electrophoresis gel tubes that contain an isoelectric focusing gel. As discussed hereinafter, transferring assembly 14 automatically removes a biological sample from supply magazine 12 and robotically transfers and delivers the sample to a respective gel tube within tanks 16.

Figure 3:
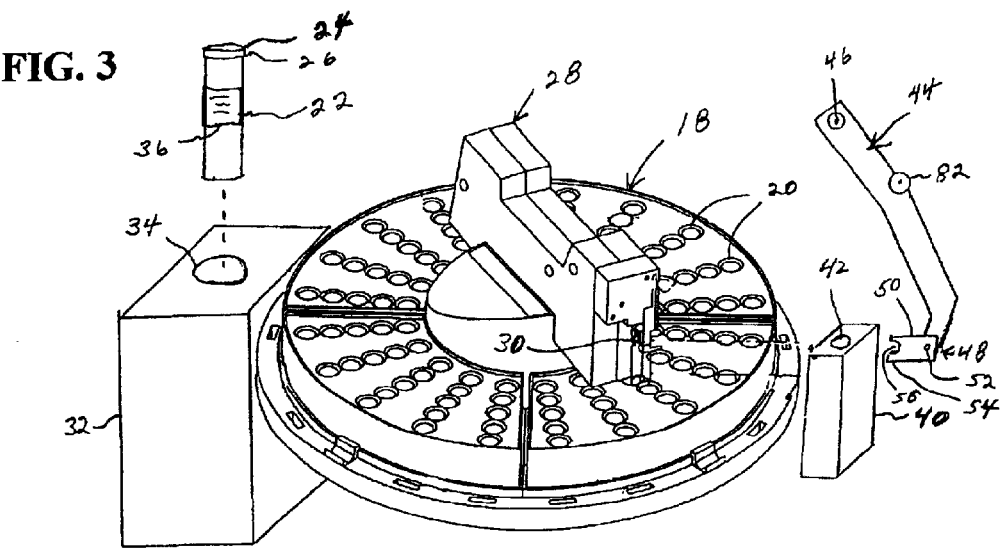
FIG. 3 is a perspective view of the supply magazine showing the carousel of the sample supply magazine, bar code reader and sample container holding device.
Figure 4:
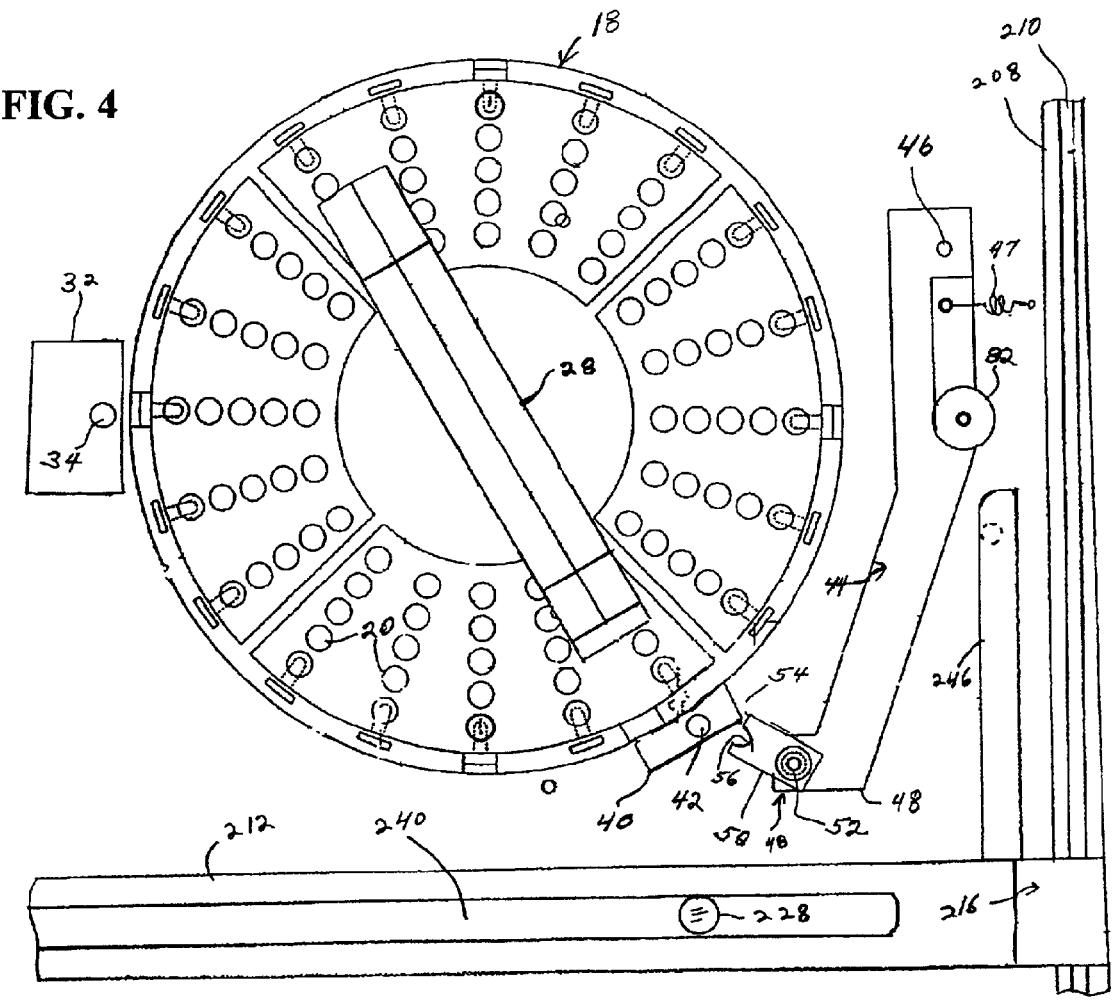
FIG. 4 is a partial top view of the apparatus of FIG. 1 showing the carousel and container retaining arm in a first position.

Referring to FIGS. 3 and 4, supply magazine 12 in a preferred embodiment is mounted on a table 13 and includes a carousel 18 having a plurality of wells 20 for storing a plurality of sample containers 22. Each sample container 22 is preferably a glass or plastic vial having an internal volume sufficient to contain a biological sample. A closure 24 is coupled to the open end 26 of sample container 22 to seal container 22 and prevent contamination of the sample and to prevent the sample from escaping. In a preferred embodiment, closure 24 is a flexible septum that can be pierced by a needle or pipette for withdrawing a sample from sample container 22.

Carousel 18 includes a robotic arm 28 that is able to pivot around the center axis of carousel 18. Carousel 18 is also able to rotate about its axis to bring a selected sample container into position for being picked up by robotic arm 28. Robotic arm 28 is able to reciprocate in a radial direction with respect to carousel 18. Robotic arm 28 includes a gripping member 30 that reciprocates in an up and down direction for gripping and removing a sample container 22 from a well 20 of carousel 18. An example of this type of carousel is manufactured by the Hewlett-Packard Corporation as the HP Automatic Liquid Sampler, Model HP 18596B.

In one embodiment of the invention, supply magazine 12 includes a bar code reader 32 positioned adjacent carousel 18 for electronically reading, storing and indexing sample information. A suitable bar code reader is made by the Hewlett-Packard Corporation, such as the reader sold as model HPG 1926A. In alternative embodiments, other devices can be used for recording and storing information relating to the samples. Bar code reader 32 includes a well 34 for receiving a sample container 22. Sample container 22 preferable includes a label 36 having a bar code or other indicia that can be read by bar code reader 32.

Referring to FIG. 1 supply magazine 12 is connected to a central processing control unit 38 (CPU) such as a computer or microprocessor for controlling the movement of robotic arm 28 and recording information from bar code reader 32. Central processing unit 38 actuates robotic arm 28 and carousel 18 to select a predetermined sample container 22 and remove sample container 22 from well 20 and transfer the container to bar code reader 32. Bar code reader 32 records the information on label 36 and stores the information for tracking and identifying a sample throughout the separation process. Bar code reader 32 is operatively connected to central processing unit 38 for recording and tracking samples as depicted schematically in FIG. 15. Supply magazine 12 also includes a sample container holding device 40 having a well 42 for receiving a sample container 22 from arm 28.

Figure 5:
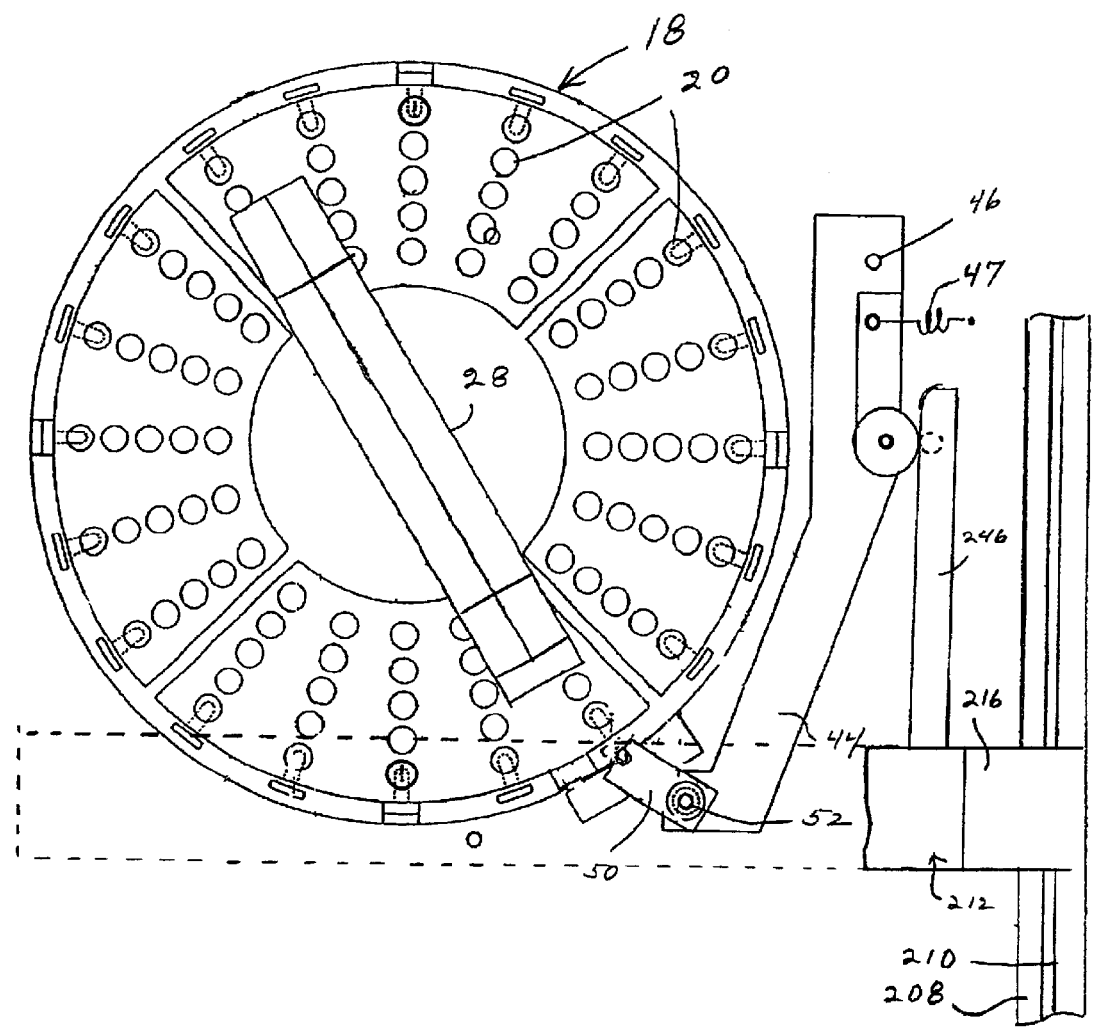
FIG. 5 is a partial top view of the apparatus of FIG. 1 showing the carousel and retaining arm in a second position for retaining a sample container in a holder.

As shown in FIGS. 3–5, holding device 40 is positioned adjacent carousel 18. Arm 28 of supply magazine 12 is able to extend to a suitable length for retrieving a sample container 22 from carousel 18 and placing the sample container 22 into well 42. Holding device 40 preferably includes a suitable mechanism for retaining sample container 22 in well 42 while the biological sample is removed from container 22.

In a preferred embodiment shown in FIGS. 3, 4 and 5, the retaining mechanism is a pivoting retaining arm 44 to hold sample container 22 within well 42. Retaining arm 44 is mounted adjacent supply magazine 12 by a pivot pin 46 to allow retaining arm 44 to pivot about the axis of pin 46 from a first position shown in FIG. 4 to a retaining position shown in FIG. 5. In the embodiment illustrated a spring 47 biases arm 44 away from supply magazine 12. Retaining arm 44 includes an operating end 48 to hold sample container 22 in well 42. In the illustrated embodiment, end 48 has an end plate 50 coupled thereto. End plate 50 is attached to retaining arm 44 by a fastener 52. Preferably, fastener 52 is a threaded screw or bolt that can be tightened to fix the position of end plate 50 with respect to retaining arm 44 and can be loosened to enable end plate 50 to pivot to enable adjustment of end plate 50 to a desired location. In this manner, end plate 50 can be adjusted on retaining arm 44 to provide proper alignment of end plate 50 with respect to holding device 40 and well 42.

As shown in FIG. 4, end plate 50 has an outer edge 54 with a substantially U-shaped recess 56. End plate 50 has a dimension sufficient to overlie the top end of a sample container 22 when received in well 42 while exposing a portion of closure 24 of sample container 22 through recess 56 for piercing closure 42 by a piercing member to remove a sample from container 22. In alternative embodiments, the retaining mechanism can be a gripping device able to grip the side walls of container 22, or a vacuum source for drawing a vacuum sufficient to hold sample container 22 within well 42. In other embodiments, plate 50 can be fixed to arm 44 or integrally formed therewith. Arm 44 can also be operated by a motor or piston and cylinder assembly, such as a pneumatic piston. A switch can be actuated by transferring assembly 14 to actuate the operating motor or pneumatic cylinder.

Figure 2:
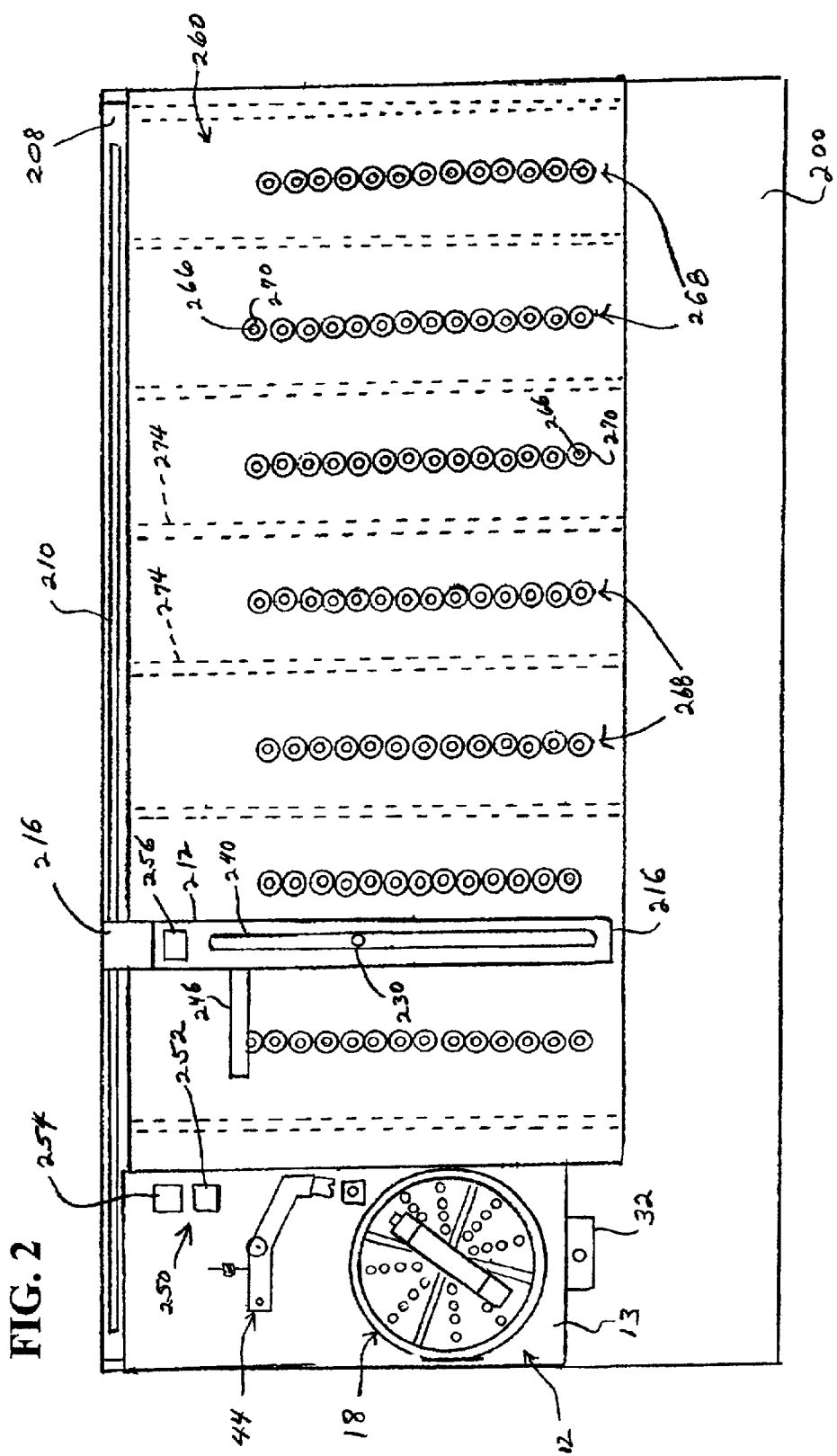
FIG. 2 is a top view of the apparatus of FIG. 1.

Referring to FIGS. 1 and 2, automated transferring assembly 14 includes a base 200 and two upright supports 202 that extend upwardly from the opposite rear corners of base 200. A support 204 extends between upright supports 202 and is coupled to a top end of each upright support 202. In the embodiment illustrated, upright supports 202 are substantially vertical and perpendicular to base 200. Support 204 is horizontal and substantially parallel to base 200. Support 204 includes a top face 208 having a track 210 extending in a longitudinal direction with respect to a longitudinal dimension of support 204 and a longitudinal dimension of assembly 14. Generally, track 210 extends substantially the entire length of horizontal support 204. In alternative embodiments, track 210 can be formed in the side or bottom of support 204.

An arm 212 is coupled to support 204 and extends outwardly therefrom toward the front edge of base 200. Arm 212 includes a first end 214 coupled to a drive and carriage assembly 216 for riding in track 210 of support 204. Drive assembly 216 includes a suitable electrical motor (not shown) for moving arm 212 in the longitudinal direction of track 214. The motor is connected to a suitable electric power source and to central processing unit 38 for controlling and operating the movement of arm 212. Drive assembly 216 can be, for example, a gear drive or chain drive assembly connected to the motor for moving arm 212 in track 210 at a controlled speed and for controlling the precise position of arm 212 in track 214 relative to support 204. In an alternative embodiment, carriage 216 can be coupled to a continuous belt that extends between two pulleys or gears at opposite ends of support 208. A dual directional drive motor can be connected to one of the pulleys to move carriage 216 along support 208.

In preferred embodiments arm 212 extends from support 204 in a substantially perpendicular direction with respect to the longitudinal dimension of support 204. In alternative embodiments, arm 212 can be at an angle less then 90 degrees with respect to the longitudinal dimension of support 204. Preferably, arm 212 is substantially parallel to base 200 and is coplanar with support 204.

Figure 6:
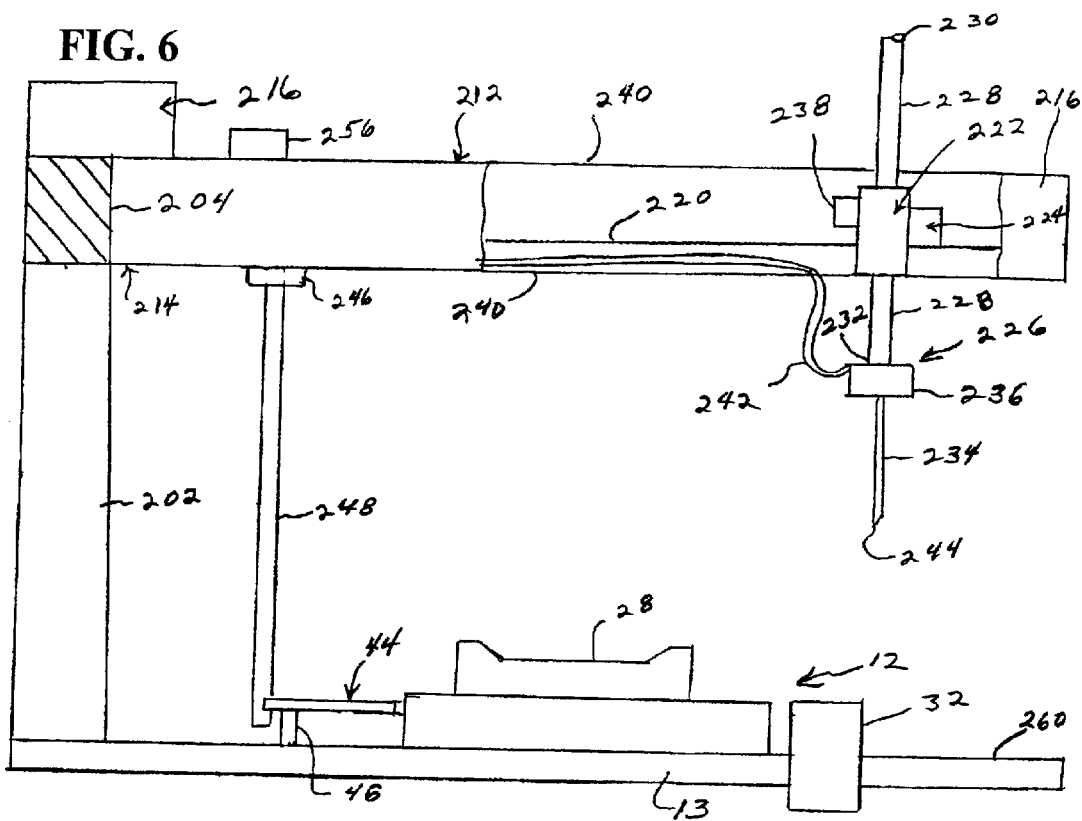
FIG. 6 is a partial side view of the apparatus of FIG. 1 showing the movable arm and the actuating member for actuating the sample container holding device.
Figure 7:
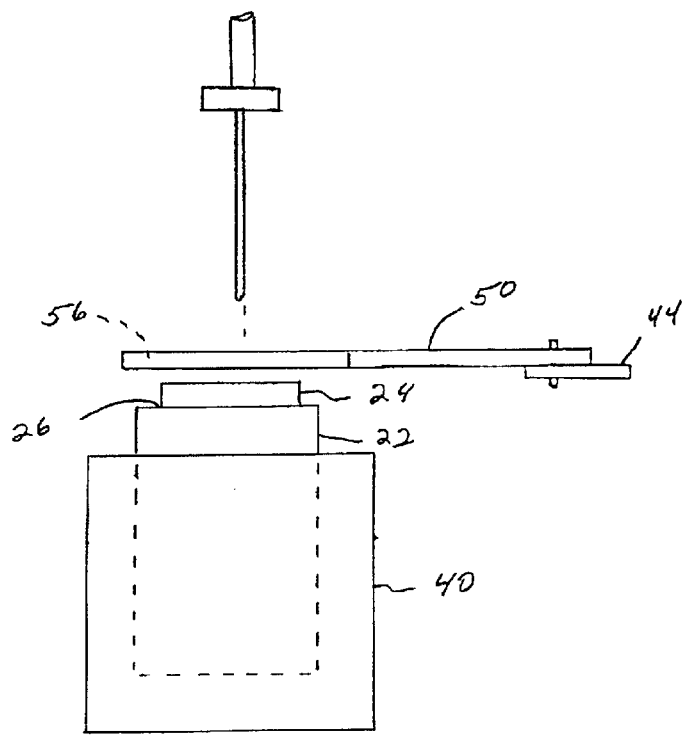
FIG. 7 is a partial side view of the sample container holding device showing the retaining arm positioned over the container.
Figure 8:
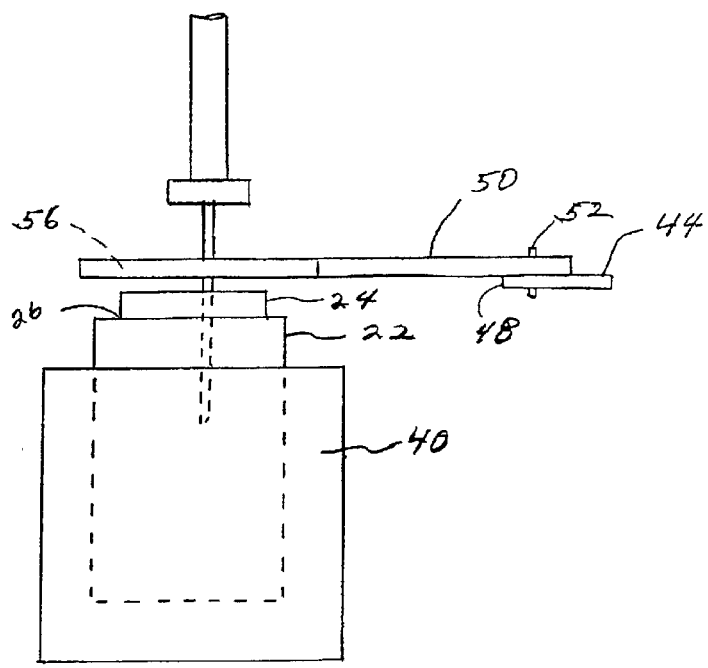
FIG. 8 is a partial front view of the sample container holding device showing the retaining arm holding the sample container in place while the pipette penetrates the septum of the sample container.

In one embodiment, arm 212 includes a track 220 enclosed within arm 212 as shown in FIG. 6. Track 220 extends substantially the entire length of arm 212 and is dimensioned to support a carriage 222 for movement along the length of arm 212 in the longitudinal direction. Carriage 222 includes a motor and drive assembly 224 as shown in FIG. 6 for moving carriage along track 220. Motor assembly 224 is connected to central processing unit 38 for controlling the movement and position of carriage on track 220. Motor and drive assembly 224 can be a gear, belt or chain drive assembly capable of moving carriage 222 along track 220. In alternative embodiments, the track can be provided on an external surface of arm 212.

In one embodiment, track 220 can have a plurality of teeth for engaging a drive gear on motor assembly 224. In an alternative embodiment, carriage 222 can be coupled to a continuous belt extending between pulleys at opposite ends of arm 212. A drive motor can be connected to one of the pulleys for moving carriage 222 along track 220.

As shown in FIG. 6, a pipette assembly 226 is coupled to carriage 222 for movement along track 220. Pipette assembly 226 includes a support rod 228 coupled to carriage 222 and is positioned in a substantially vertical direction. Support rod 228 has a longitudinal dimension with a top end 230 and a bottom end 232. A pipette 234 having a control valve member 236 is coupled to bottom end 232 of support rod 228. Support rod 228 extends through carriage 222 and is coupled to a drive motor 238 for raising and lowering support rod 228 in a vertical direction with respect to arm 212. In one embodiment of the invention support rod 228 includes external teeth for engaging a gear on motor 238 for raising and lowering support rod 228 with respect to arm 212. Drive motor 238 is also connected to central processing unit 38 for operating support rod 228 as discussed hereinafter in greater detail. As shown in FIGS. 2 and 6 arm 212 includes an upper and lower longitudinal slot 240 extending the length arm 212 for allowing carriage 222 and support rod 228 to move along track 220. In alternative embodiments carriage 222 for pipette assembly 226 can be mounted on an external surface of arm 212.

Control valve member 236 preferably is an electrically operated valve for opening and closing pipette 234 to withdraw or dispense a liquid sample. Control valve member 236 and pipette 234 are coupled to a suitable pump through a flexible tube 242 for selectively providing a vacuum source and a pressure source for selectively withdrawing a liquid sample from sample container and dispensing the sample to a gel tube. Control valve member 236 and the pump are also connected to the central processing unit for operating pipette assembly 226.

In preferred embodiments, pipette 234 is a hollow needle-like device having an axial length to be inserted into a supply container for withdrawing a liquid sample and for being inserted into or onto the end of a gel tube for dispensing the sample onto the open end of the gel tube. Typically pipette 234 is made of stainless steel or other materials that do not interfere with the sample materials. Preferably pipette 234 has an internal volume sufficient to contain a volume of a sample for conducting the electrophoresis separation without drawing the sample into the tube 242. Since the required volume of a biological sample is quite small, pipette 234 is able to relieve a suitable volume for electrophoresis separation. In preferred embodiments pipette 234 has a sharpened tip 244 capable of penetrating the septum of a sample container so that a sample can be removed from a sample container without opening the sample container.

Referring to FIGS. 1, 2 and 6, a support member 246 is coupled to arm 212 and extends in a direction substantially parallel to the longitudinal dimension of support 204. In the embodiment illustrated support member 246 is substantially parallel to base 200. An actuator rod 248 is coupled to support member 246 and extends in a downward direction toward base 200. As shown in FIG. 6 actuator rod 248 is aligned with holding device 44 for moving arm 48 into the retaining position for retaining a sample container in the well 42.

As shown in FIG. 1, transferring assembly 14 is coupled to central processing unit 38 for controlling the movement of movable arm 212, carriage 222 and for operating pipette assembly 226. In operation, sample containers 22 containing a biological sample are provided in carousel 18. A sample container 22 is selected and grasped by arm 28 of carousel 18 and placed in bar code reader 32 where the sample identification and other information is recorded and stored in central processing unit 38. Arm 28 of carousel 18 then transfers sample container 22 from bar code reader 32 to holding device 40. Retaining arm 44 of supply magazine 12 is positioned in the horizontal path of actuator arm 248. As shown in FIG. 6, actuator rod 248 of arm 212 is moved into contact with retaining arm 44 to pivot retaining arm 44 into the retaining position.

As shown in FIGS. 3 and 4, retaining arm 44 includes a bearing 82, such as a roller bearing, for contacting actuator arm 248. Retaining arm 44 also includes a biasing member, such as a spring 47, to bias retaining arm 44 outwardly from carousel 18 to the position shown in FIG. 4. As arm 212 is moved toward supply magazine 12 actuator arm 248 contacts bearing 82 causing retaining arm 44 to pivot about pivot pin 46 so that the end plate 50 overlies the sample container 22 as shown in FIG. 5 with U-shaped recess 56 oriented over closure 24. Pipette assembly 226 is lowered to a position where pipette 234 pierces closure 24 of sample container 22. Pump 80 is actuated to withdraw a desired amount of a sample from container 22 into pipette 234. Pipette assembly 226 is then raised to withdraw pipette 234 from sample container 22. End plate 50 of retaining arm 44 overlies sample container 22 to hold sample container 22 in holding device 40 while pipette 234 is withdrawn. Retaining arm 44 prevents sample container 22 from being lifted upward when pipette 68 is raised to the upper position.

Arm 212 and pipette assembly 226 are then moved along horizontal track 210 to a selected position corresponding to a designated gel tube in an electrophoresis tank 16. As arm 212 is moved away from supply magazine 12, actuator arm 248 disengages retaining arm 44, allowing arm 44 to pivot outward from carousel 18. Pipette assembly 226 is then lowered to a position at the top end of the designated gel tube and pump 256 is actuated to dispense the sample from pipette 234 onto the top end of the gel tube. Pipette assembly 236 is then raised and arm 212 is moved along horizontal track 210 to a rinsing station 250 for rinsing sample residue from pipette 234.

Rinsing station 250 includes a container 252 containing a rinsing liquid such as distilled water. Pipette assembly 226 is lowered to insert pipette 234 into container 252 where a sufficient amount of the rinsing liquid is drawn into pipette 236 to rinse the inner surfaces of pipette 236. Pipette 236 is then raised and moved to a position above a discharge container 254 where the rinsing liquid is discharged. Generally, a single rinsing cycle is sufficient to clean the residue from pipette 234.

Arm 212 and pipette 236 are then moved back to the position shown in FIG. 5 and the steps repeated to transfer another sample from a sample container to a designated gel tube. The sequence of steps is repeated until the desired samples from the sample containers are transferred to a designated gel tube. Control unit 38 controls the movement of the supply magazine and transferring assembly 14 and records the location of each sample to identify a sample with a particular gel tube.

Assembly 10 includes a planar cover member 260 that is coupled to supports 202 at a rear edge thereof. Side supports 262 extend from the longitudinal ends 264 of cover member 260 to support the front and sides of cover member 260. As shown in FIGS. 1 and 2 cover member 260 is substantially parallel to base 200. Cover member 260 is dimensioned to overlie each electrophoresis tank 16 and is spaced from base 200 a distance to effectively close a top end of each electrophoresis tank 16. As shown in FIG. 1 each electrophoresis tank 16 fits below cover member 260.

Figure 12:
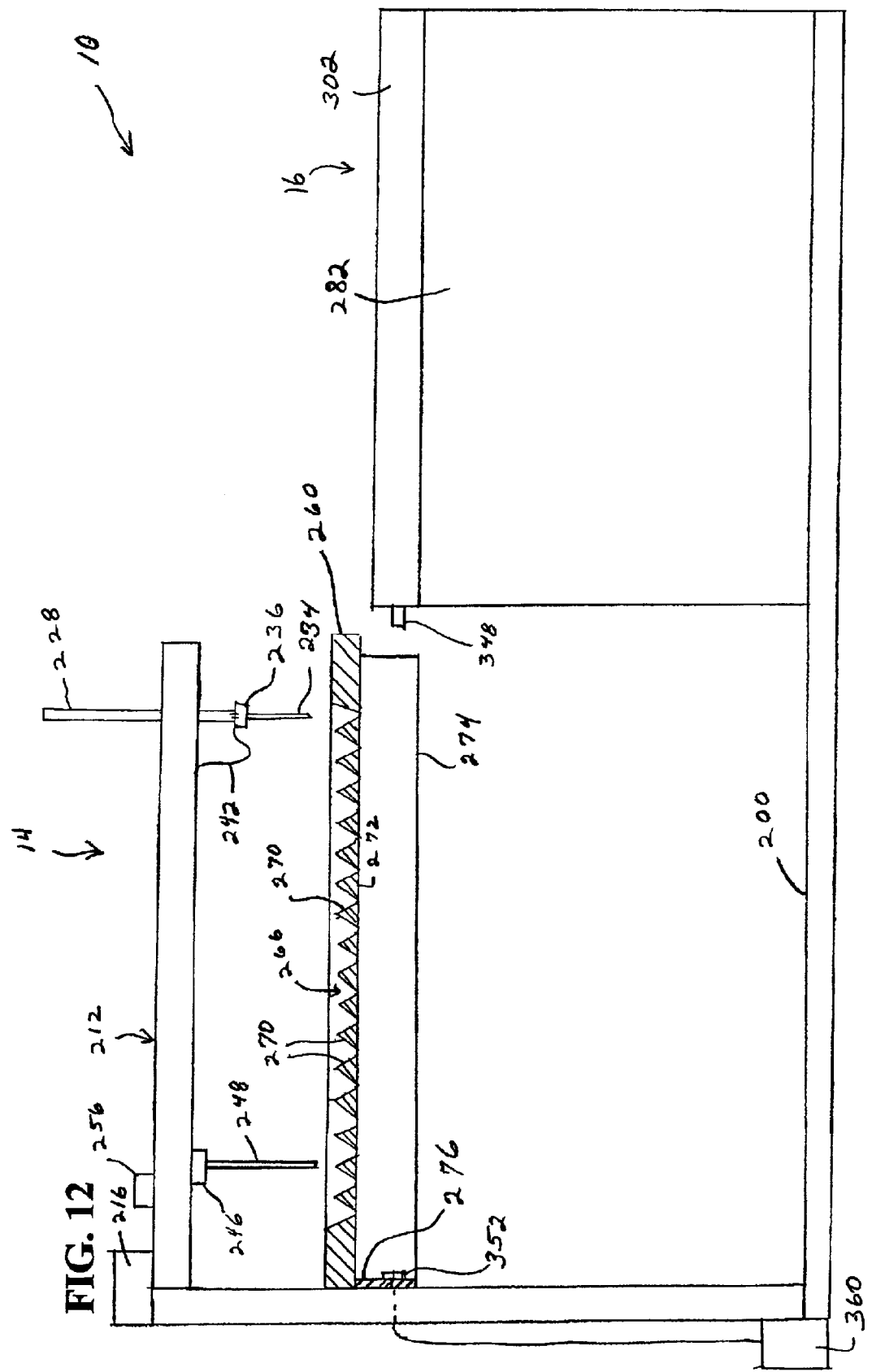
FIG. 12 is an end view of the apparatus of FIG. 1 showing the electrophoresis tank and the apertures in the cover member for guiding the pipette into the gel tubes in the electrophoresis tank and showing the pipette in the raised position.

Cover member 260 includes a plurality of apertures 266 oriented in parallel rows 268. In a preferred embodiment of the invention rows 268 extend in a direction substantially perpendicular to the longitudinal dimension of support 204 and parallel to the longitudinal dimension of arm 212. The number of apertures 266 in each row 268 correspond to the number of gel tubes in each electrophoresis tank 16 and are spaced apart to distance corresponding to the spacing between the gel tubes. As shown in FIG. 12 apertures 266 extend through cover member 260 and have inclined surfaces that converge to a bottom surface 272 of cover member 260. In the embodiment illustrated, the inclined surfaces form a substantially frustoconical shaped top surface 270. Frustoconical surfaces 270 are dimensioned to guide pipette 234 through apertures 266.

A plurality of guide rails 274 are coupled to bottom surface 272 of cover member 260 as shown in FIGS. 1 and 2. Guide rails 274 extend in a direction substantially parallel to rows 268 of apertures 266. In preferred embodiments of the invention guide rails 274 are oriented and spaced apart a distance to accurately position each electrophoresis tank 16 below cover member 260 so that each gel tube is positioned directly below a respective aperture 266. An end wall 276 extends between adjacent guide rails 274 at a rear end of cover member 260 as shown in FIG. 12. Guide rails 274 and end wall 276 serve as a guide assembly to position electrophoresis tank 16 for aligning the gel tubes with a respective aperture 266.

Figure 9:
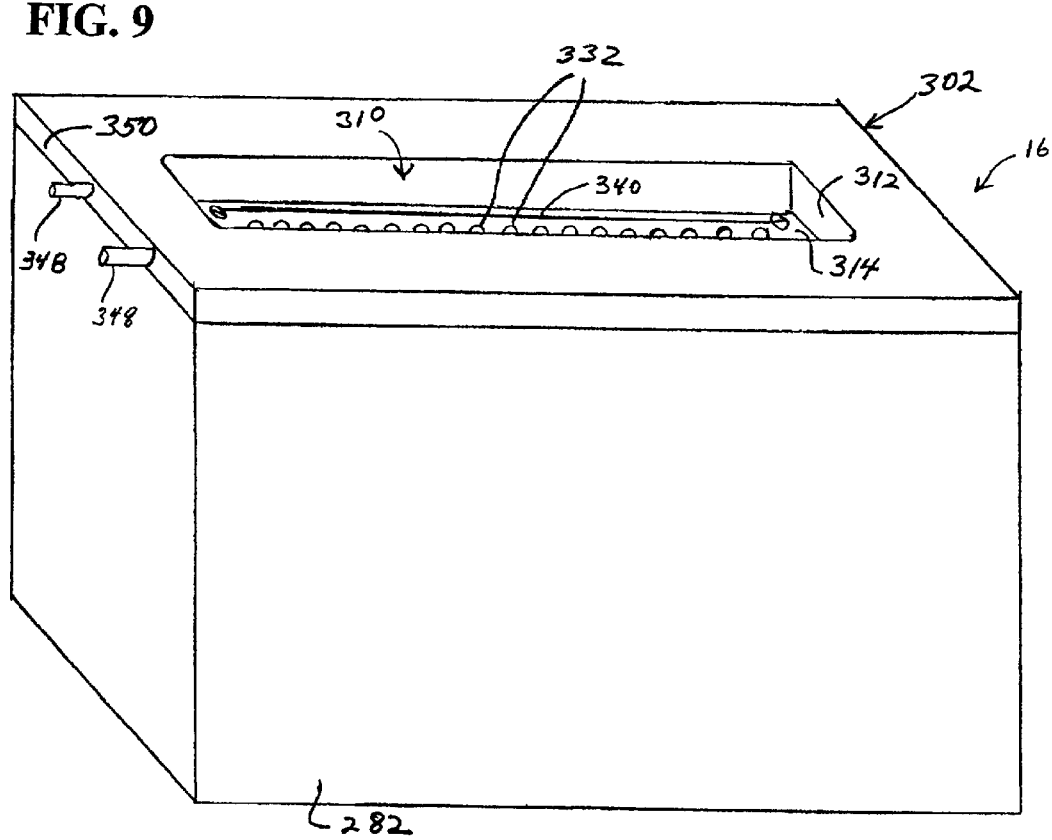
FIG. 9 is perspective view of the electrophoresis tank and gel tube rack.
Figure 10:
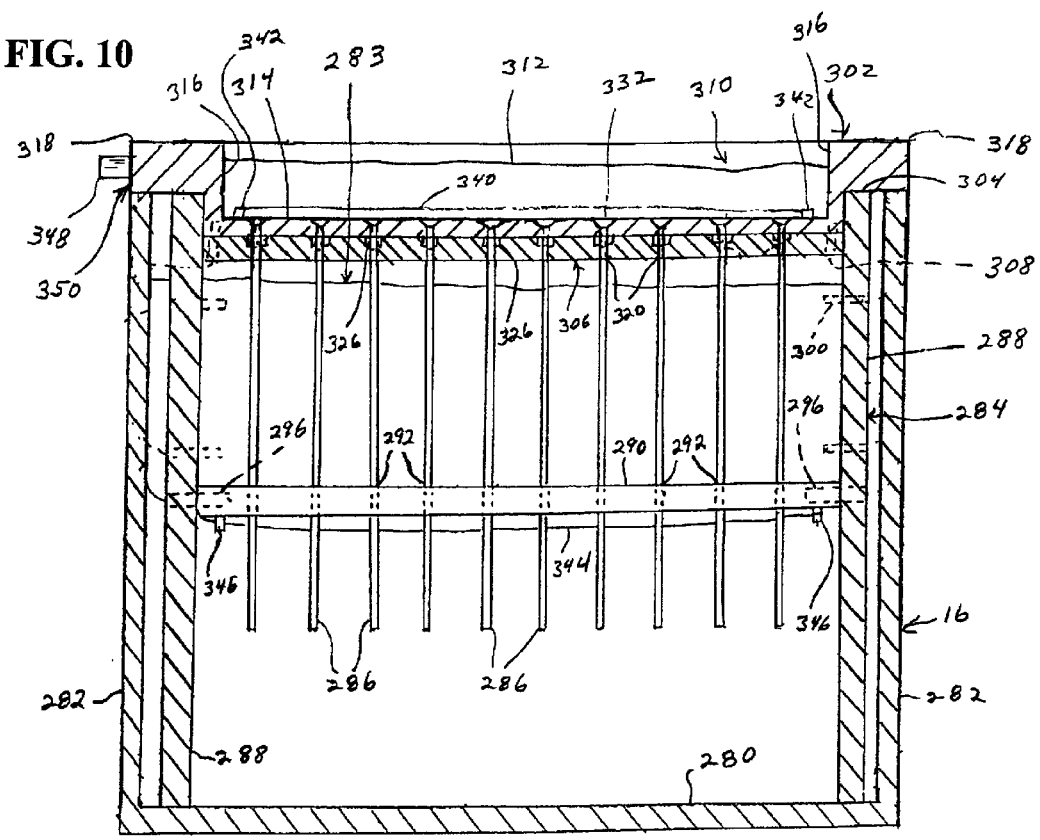
FIG. 10 is a front cross sectional view of the gel tube rack positioned in the tank in one embodiment of the invention.

Referring to FIGS. 9–14, electrophoresis tanks 16 have a bottom wall 280 and side walls 282 for containing a first buffer solution 283. A rack 284 supporting a plurality of gel tubes 286 is dimensioned to fit within each tank 16 as shown in FIG. 10. In one embodiment of the invention, bottom wall 280 of tank 16 can include an optional spacing member such as a pair of blocks for positioning rack 284 within tank 16 in a predetermined location. Preferably, tank 16 and rack 284 are dimensioned to fit between guide rails 274 and below cover member 260 with only minimal clearance. In this manner, rack 284 and gel tubes 286 are oriented in a precise location with respect to cover member 260 so that pipette 234 of transferring device 14 can transfer a biological sample from a sample container 22 to a designated gel tube 286 in successive runs without the need to recalibrate the apparatus after each run. In a preferred embodiment, gel tubes 286 are oriented in a straight row and spaced apart a distance corresponding to the spacing of apertures 266 in cover member 260.

Figure 13:
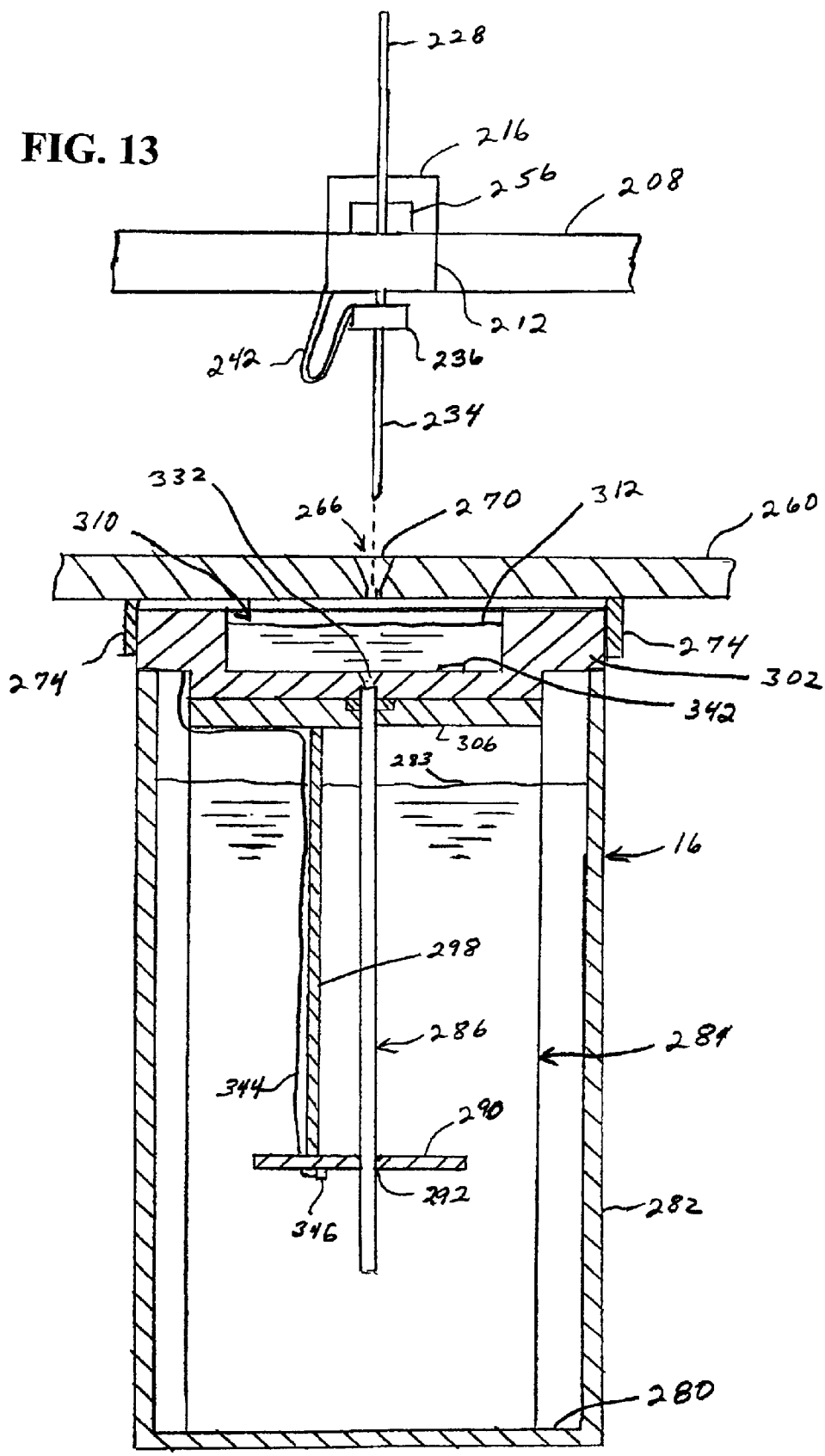
FIG. 13 is a partial cross sectional view of the apparatus of FIG. 8 with the electrophoresis tank positioned below the cover member and showing the pipette in the raised position above a gel tube.

Rack 284 in the embodiment illustrated, has a pair of side walls 288 spaced apart a sufficient distance to enable rack 286 to fit within tank 16. Side walls 288 function as a support for rack 286 when positioned in tank 16. A lower brace 290 extends between side walls 288 to stabilize rack 284. A plurality of spaced apart holes 292 having a conical surface are formed in brace 290 to support tubes 286 as shown in FIG. 10. Preferably, brace 290 is a planar member extending perpendicular to side walls 288 to lie in a substantially horizontal plane when rack 284 is positioned in tank 16. Brace 290 is coupled to side walls 288 by screws 296 or other suitable fasteners. A vertical brace 298 extends between side walls 288 and is coupled thereto by screws 300 or other suitable fasteners to further stabilize rack 284 as shown in FIGS. 10 and 13.

Figure 11:
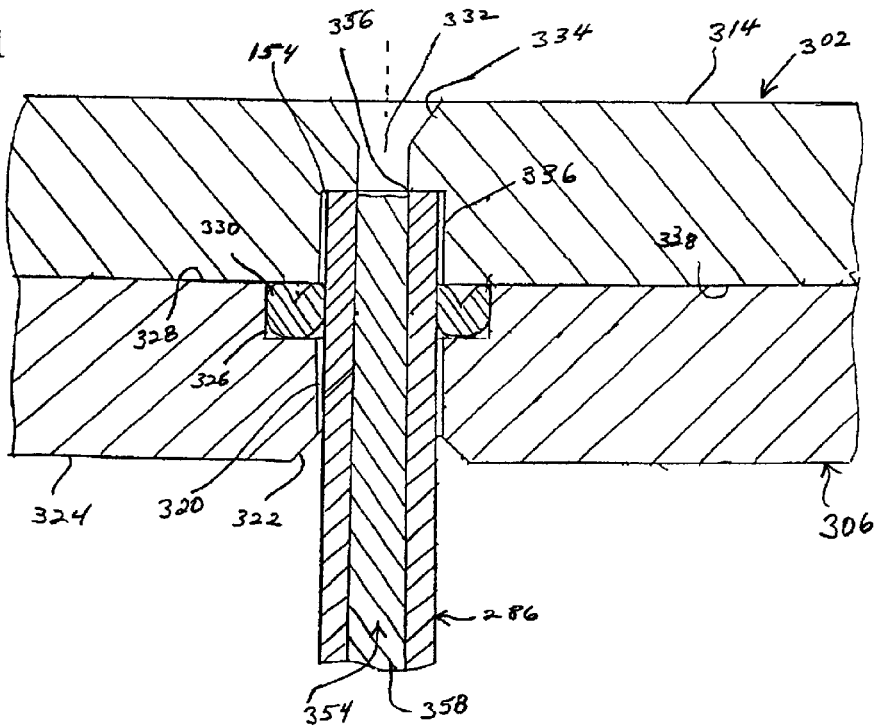
FIG. 11 is a partial enlarged view in cross section of the rack showing the gasket for holding the gel tube in place.

Rack 284 includes a top member 302 coupled to a top end 304 of side walls 282. Top member 302 includes a lower plate 306 coupled together by screws 308. Top member 302 includes a well 310 that is dimensioned to contain a sufficient amount of a second buffer solution 312 for conducting electrophoresis separation as known in the art. Well 310 is formed by a bottom wall 314 and side walls 316. A ledge 318 extends outwardly from said walls 316 and is dimensioned to overlie the top end of side walls 282 of tank 16. Lower plate 306 is oriented in a substantially horizontal position and parallel to bottom wall 314. As shown in FIGS. 10 and 11, lower plate 306 is provided with a plurality of spaced apart openings 320 that are dimensioned to receive gel tubes 286. Openings 320 have a conical recess 322 on a bottom face 324 of plate 306 for guiding gel tubes 286 into openings 320. Plate 306 also includes an annular recess 326 on a top face 328 surrounding each opening 320 for receiving an annular gasket 330 having a substantially V-shaped cross-section.

Bottom wall 314 of well 310 includes a plurality of openings 332 having a conical shaped inlet end 334. An annular recess 336 is formed in a bottom face 338 of bottom wall 314. Annular recess 336 is dimensioned to receive the end of gel tube 286 as shown in FIG. 11.

As shown in FIGS. 9 and 10, a first electrode 340 is provided within well 310 and secured in place by screws 342. In a preferred embodiment of the invention, first electrode 340 is a wire that extends substantially the length of well 310. As shown in FIG. 10, a second electrode 344 extends along brace 290 and is secured in place by mounting screws 346. Electrode 344 is coupled to rack 284 in a position to be immersed in buffer solution 283.

As shown in FIG. 10, ledge 318 of top member 302 is spaced from the bottom end of side walls 288 a distance corresponding substantially to the height of side walls 282 of tank 16. In this manner, ledge 318 is able to rest on an upper end of side wall 282 with side walls 288 of rack 284 supported by bottom wall 280 of tank 16. In one embodiment, alignment pins are provided in ledge 318 that are received in a respective recess formed in the top end of side wall 282 to orient rack 284 within tank 16. In a preferred embodiment, the pins are spring loaded pins commonly referred to as "banana clips".

In a preferred embodiment, two electrical contacts 348 in the form of pins extend outwardly from an end 350 of top member 302 as shown in FIGS. 9 and 10. Contact pins 348 are made of metal or other electrically conducting material. Electrodes 340 and 344 are connected to a respective contact pin 348. End wall 276 at the end of guide rails 274 include two complementary contacts 352 having recesses for receiving contact pins 348. Contacts 352 are connected to a suitable electric power source to apply an electric potential to electrodes 340 and 344. Rack 284 is positioned between guide rails 274 and end 350 of ledge 318 rests against end wall 276 to enable contact pins 348 to engage contacts 352.

Referring to FIG. 11, gel tubes 286 have a cylindrical shape with a central passage 354 and open ends 356. The inner dimension of gel tubes 286 can range from 0.5 mm to about 2 mm and can be about 20 cm long. Gel tubes 286 are standard gel tubes as known in the electrophoresis art. An electrophoresis gel 358 is placed in gel tubes 286 to substantially fill the internal dimension as shown in FIG. 11 by known techniques. The gel forming materials can be placed in the tube and polymerized to form the gel. The gels can be IPG gels or other isoelectric focusing gels as known in the art.

The electrophoresis separation process of the invention is carried out using the apparatus 10. Gel tubes 286 containing a gel 358 are mounted in rack 284 by sliding gel tubes 286 through the holes 292 in lower brace 290. A conical surface of the holes 292 in lower brace 290 provide a guiding surface for guiding gel tubes 286 through brace 290. Gel tubes 286 are then inserted into openings 320 of lower plate 306 using conical recesses 322 as a guide. The top end of gel tube 286 is seated in recess 336 of the bottom face of bottom wall 314 as shown in FIG. 11. Annular gasket 330 is dimensioned to provide a fluid tight seal around gel tube 286 to prevent fluids from passing from well 310 into tank 16.

A buffer solution 283, such as a phosphoric acid solution, is provided in tank 16. Rack 286 is positioned in tank 16 with a buffer solution 283 maintained at a level above the lower end of gel tubes 286 and electrode 340. A second buffer solution 312, such as a sodium hydroxide solution, is placed in well 310 to a sufficient level to cover the top end of gel tubes 286 and electrode 340. Tank 16 is positioned between guide rails 274 to position each gel tube 286 directly below an aperture 266 in cover member 260.

Transferring assembly 14 is actuated to transfer a biological sample from supply magazine 12 to a respective gel tube 286. Pipette 234 withdraws a biological sample from a sample container 22 as previously discussed. Arm 212 moves along track 210 to a location above a respective gel tube 286 as shown in FIG. 13. The conical surface 270 of aperture 266 guides pipette 234 through aperture 266 and directly to the top end of gel tube 286. The conical surface 270 of apertures 266 forms a guide surface to compensate for misalignment of pipette 234 with aperture 266. Although microprocessor 38 and the consistent location of gel tubes 286 usually provide proper alignment of pipette 234, misalignment can occur as a result of the pipette tip being bent or distorted. Repeated piercing of the septum of the sample containers can bend pipette 234, thereby causing the tip to be misaligned with the apertures 266 in cover 260. Conical surfaces 270 can assist in aligning and directing the tip of pipette 234 to the proper location above gel tubes 286.

Figure 14:
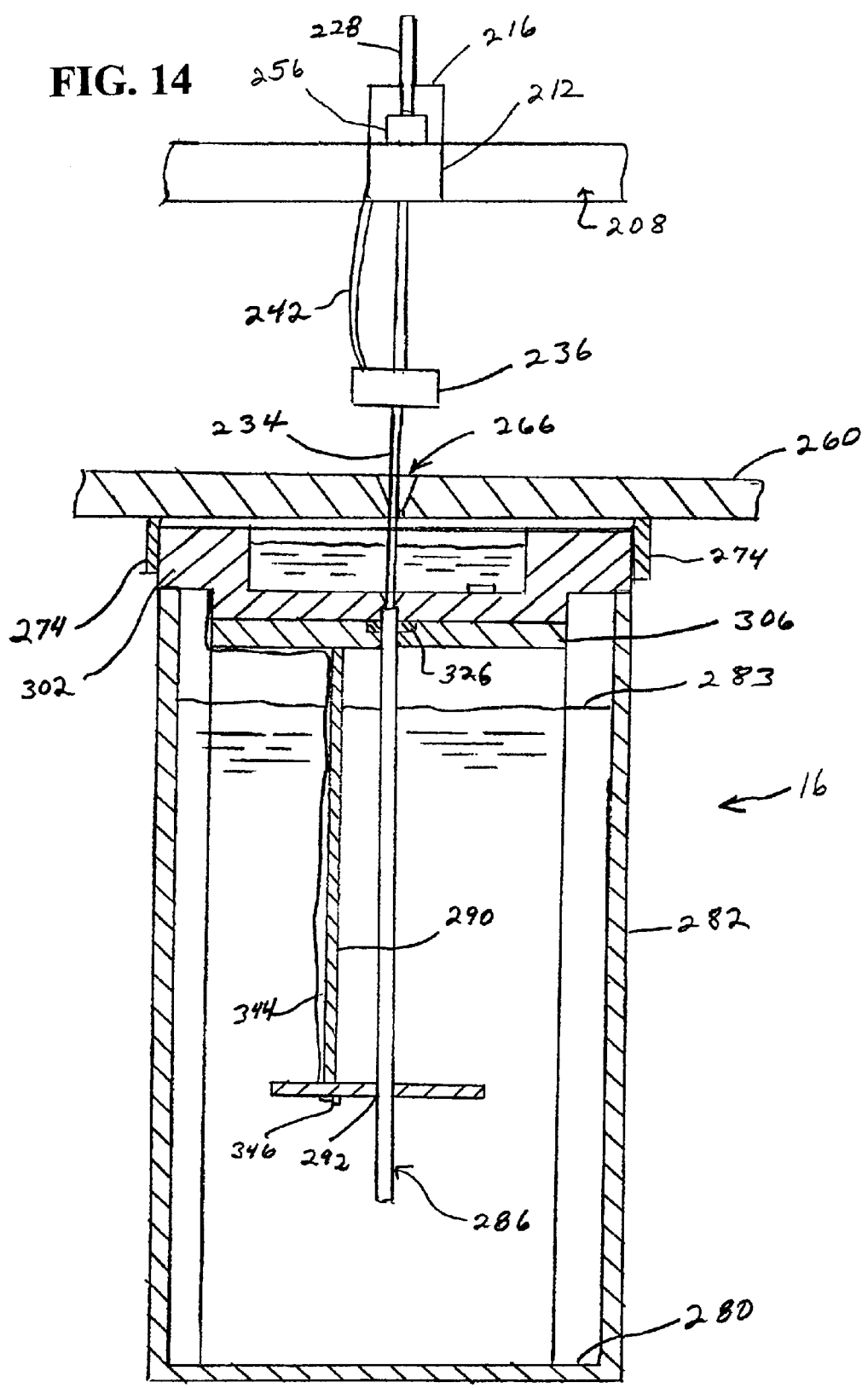
FIG. 14 is a partial cross-sectional view of the tank and gel tube rack showing the pipette in the lowered position for transferring a sample into a gel tube.

As shown in FIG. 13, apertures 266 of cover 260 are axially aligned with openings 320 and gel tube 286. As shown in FIG. 14, pipette assembly 226 is moved downward to insert the lower end of pipette 234 to the top end of gel tube 286. Pipette 234 then dispenses the biological sample onto the top end of the gel in gel tube 286. Pipette 234 is removed and returned to supply magazine 112 to repeat the process.

After a biological sample is placed on the top end of each gel tube 286, contacts 252 are connected to a suitable power source 360 for applying an electric current to the electrodes and the buffer solutions. The electric current causes the various molecules of the biological sample to migrate through the gel tube as in standard first dimension electrophoresis separation. After a predetermined period of time, gel tubes 286 are removed from rack 284 and the gels are transferred to a second dimension separation apparatus as known in the art.

In preferred embodiments, power source 260 is operatively connected to central processing unit 38. Central processing unit 38 controls the voltage applied between the electrodes 340, 344 of tank 16. The current and voltage fluctuations are measured, continuously monitored and recorded over time throughout the duration of the isoelectric focusing to provide information for quality control. The recorded voltage and current can then be plotted as a function of time throughout the process.

Figure 15:
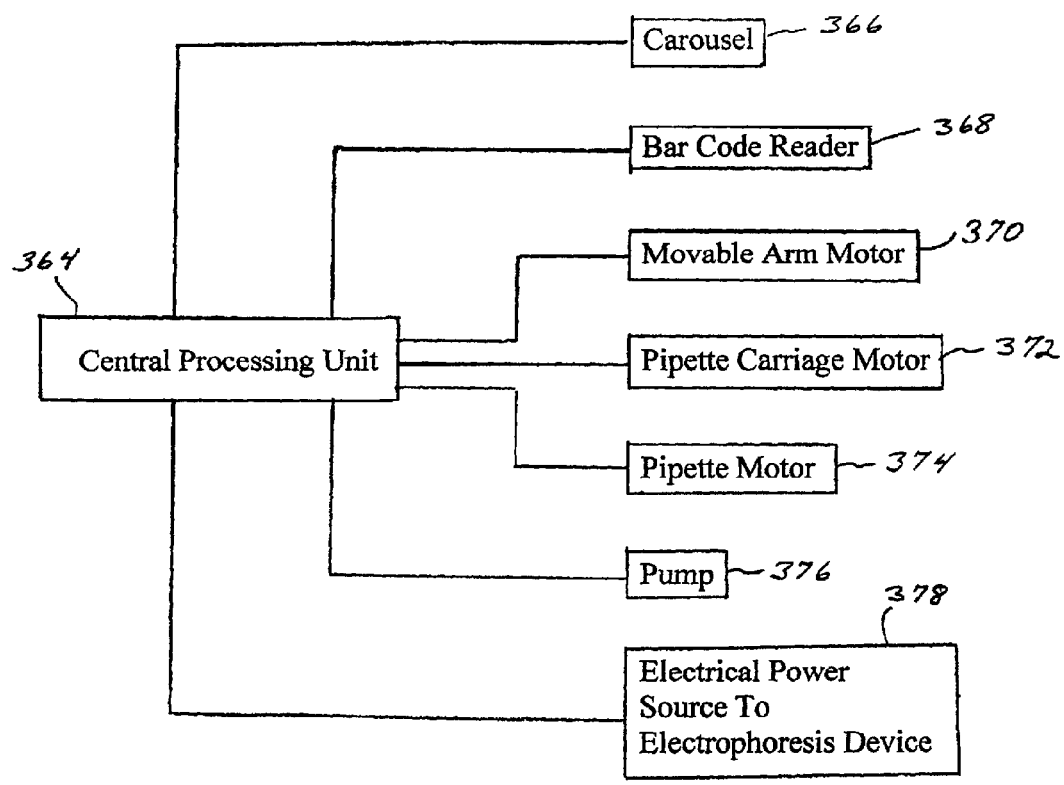
FIG. 15 is a schematic diagram of the assembly control system.

FIG. 15 is a schematic diagram of the control system for coordinating the various operations discussed above. As shown, a central processing unit or computer indicated by block 364 is operatively connected to the carousel indicated by block 366 and bar code reader indicated by block 368 for recording data relating to each sample being processed. The movable arm motor indicated by block 370, pipette carriage motor indicated by block 372 and pipette motor indicated by block 374 are connected to an controlled by the central processing unit. A pump indicated by block 376 is operatively connected to the central processing unit to control the operation of the pipette. A power source indicated by block 378 is also connected to the control processing unit to control the electrophoresis separation process.

A temperature control device is preferably provided with the tanks for measuring and adjusting the temperature of buffer solutions. The temperature control device is able to provide heating or cooling to the tank to maintain the temperature within a predetermined range. Preferably, temperature control device is connected to and controlled by central processing unit 38 through a suitable connection.

While various embodiments of the invention have been illustrated, it will be understood by those skilled in the art that additions and modifications can be made without departing from the scope of the invention as set forth in the appended claims.

What is claimed is:

1. An automated first dimensional electrophoresis separation apparatus comprising:
   an electrophoresis assembly supporting a plurality of gel tubes containing an electrophoretic gel, each of said tubes having a first open end and second open end;
   a supply magazine for containing a plurality of sample containers, each sample container containing a sample to be subjected to electrophoresis;
   a transferring device for sequentially removing a sample from a preselected sample container and transferring said sample to a first end of a respective gel tube, said transferring device including a pipette that is movable in three dimensions between said supply magazine and a gel tube of said electrophoresis assembly; and
   a microprocessor operatively connected to said transferring device to automatically control the transfer of said sample to said respective gel tube.

2. The apparatus of claim 1, wherein said transferring device includes a first horizontal support extending in a first longitudinal direction with respect to a longitudinal dimension of said assembly, and an arm coupled to said first support and extending in a second direction, and wherein said arm is movable along said first support in said first direction.

3. The apparatus of claim 2, wherein said pipette is coupled to said arm and movable along said arm in said second direction.

4. The apparatus of claim 3, wherein said pipette is mounted for reciprocal movement along a vertical axis in a vertical direction with respect to said assembly.

5. The apparatus of claim 2, wherein said electrophoresis assembly is spaced from said supply magazine in said first direction, and wherein said gel tubes are aligned in a row extending in said second direction.

6. The apparatus of claim 1, wherein said electrophoresis assembly comprises a plurality of electrophoresis tanks, each of said tanks having a plurality of said gel tubes arranged in rows oriented in said second direction.

7. The apparatus of claim 1, further comprising a substantially horizontal cover coupled to said apparatus wherein said electrophoresis assembly is positioned below said cover.

8. The apparatus of claim 7, wherein said cover includes a plurality of apertures aligned with said gel tubes in said electrophoresis assembly.

9. The apparatus of claim 8, wherein said cover has a top surface, a bottom surface, and a guide assembly coupled to said bottom surface for positioning said electrophoresis device and said gel tubes in a selected position with respect to said apertures in said cover.

10. The apparatus of claim 9, wherein said guide assembly comprises a pair of spaced apart parallel guide rails and a stop member positioned at one end of said guide rails, said stop member being positioned to align said gel tubes with said apertures in said cover.

11. The apparatus of claim 8, wherein said cover has a top surface with a frustoconical recess surrounding each of said apertures in said cover for guiding said pipette through said apertures.

12. The apparatus of claim 9, wherein said electrophoresis assembly includes a tank for containing a first buffer solution, a rack supporting said gel tubes and being positionable in said tank, said rack having a top surface with a well for containing a second buffer solution, said rack further having a plurality of passages for receiving said gel tubes and positioning said first end of said gel tubes in said well and said second end in said first buffer solution.

13. The apparatus of claim 12, wherein said rack includes a first electrode for contacting said first buffer solution and being connected to a first electrical contact, said rack including a second electrode for contacting said second buffer solution and being connected to a second electrical contact, and wherein said guide assembly includes first and second electrical contacts for contacting said first and second electrical contacts of said rack for supplying electrical current to said electrodes.

14. The apparatus of claim 1, wherein said electrophoresis assembly includes a plurality tanks, each of said tanks having a rack supporting a plurality of said gel tubes in a row, and wherein said apparatus includes a horizontal cover member having a plurality of spaced apart rows of apertures, a plurality of guide members coupled to said cover member and positioned between said rows for positioning said tanks below said cover member whereby said apertures in said cover member are aligned with a respective gel tube.

15. An automated first dimension electrophoresis separation assembly comprising: an electrophoresis assembly including at least one tank and a plurality of gel tubes vertically supported in said tank and arranged in a row, said gel tubes having an open top end; a supply magazine for containing a plurality of sample containers, each of said sample containers containing a liquid sample; a movable arm movable in a substantially linear horizontal first direction between said supply magazine and said electrophoresis assembly; and a movable pipette coupled to said arm and being movable along a longitudinal dimension of said movable arm in a second direction, said pipette further being movable in a vertical direction, with respect to said movable arm, wherein said pipette is movable from a first position for removing a sample from a sample container to a second position for dispensing a sample in a respective gel tube.

16. The assembly of claim 15, further comprising a first support member extending in a longitudinal dimension of said assembly, and wherein said movable arm is coupled to said first support member and being movable along said first support member.

17. The assembly of claim 16, wherein said movable arm extends substantially perpendicular to said first support member.

18. The assembly of claim 16, comprising a first drive motor operatively connected to said movable arm for moving said movable arm along said first support member.

19. The assembly of claim 15, further comprising a microprocessor operatively coupled to said movable arm and said pipette for operating said movable arm and said pipette.

20. The assembly of claim 18, further comprising a second drive motor operatively connected to said pipette for moving said pipette in a vertical direction with respect to said movable arm.

21. The assembly of claim 20, further comprising a support rod having a longitudinal axis and a lower end, said support rod being coupled to said movable arm and being movable in said vertical direction, wherein said pipette is coupled to said lower end of said support rod.

22. The assembly of claim 21, wherein said second drive motor is operatively connected to said support rod for moving said support rod in said vertical direction with respect to said movable arm.

23. The assembly of claim 22, wherein said movable arm includes a longitudinal track and a carriage movable along said track, said second drive motor and said support rod being operatively connected to said carriage for movement along said track.

24. The assembly of claim 15 further comprising a stationary cover member positioned above said electrophoresis assembly, said cover assembly having a top surface and a bottom surface and a plurality of apertures extending between said top surface and said bottom surface, said apertures being arranged in a row and being aligned with said gel tubes.

25. The assembly of claim 24, wherein said row of gel tubes and said row of said apertures extend substantially parallel to said longitudinal dimension of said movable arm.

26. The assembly of claim 25, wherein said cover member includes a guide assembly coupled to said bottom surface of said cover member.

27. The assembly of claim 26, wherein said guide assembly comprises a pair of spaced apart guide rails for positioning said electrophoresis assembly and aligning said gel tubes with said apertures in said cover member.

28. The assembly of 27, further comprising a stop member extending between said guide rails at one end thereof.

29. The assembly of claim 28, further comprising a pair of electrical contacts coupled to said stop member for supplying an electric current to said electrophoresis assembly.

30. The apparatus of claim 29, wherein said electrophoresis assembly includes a rack supporting said gel tubes and being positionable in said tank, said rack having a top surface with a well for containing a second buffer solution, said rack further having a plurality of passages for receiving said gel tubes and positioning said top end of said gel tubes in said well.

31. The apparatus of claim 30, wherein said rack includes a first electrode for contacting said first buffer solution and being connected to a first electrical contact, said rack including a second electrode for contacting said second buffer solution and being connected to a second electrical contact, and wherein said first and second electrical contacts of said stop member are positioned for contacting said first and second electrical contacts of said rack for supplying electrical current to said electrodes.

32. The apparatus of claim 15, wherein said electrophoresis assembly includes a plurality of tanks, each of said tanks having a rack supporting a plurality of said gel tubes in a row, and wherein said apparatus includes a horizontal cover member having a plurality of spaced apart rows of apertures, a plurality of guide members coupled to said cover member and positioned between said rows to position said tanks below said cover member whereby said apertures in said cover member are aligned with a respective gel tube.

33. An apparatus for loading a biological sample into an electrophoresis device, said apparatus comprising:
  a vertical support;
  a stationary cover member having a top surface, a bottom surface and being coupled to said support, said cover member having a plurality of apertures arranged in a plurality of spaced apart rows;
  said bottom surface of said cover member being positioned to receive a plurality of electrophoresis devices;
  a supply magazine for containing a plurality of sample containers containing a biological sample;
  a robotic arm movable between said supply magazine and a selected aperture of said cover member, said robotic arm having a pipette for withdrawing a sample from a sample container and delivering said sample to said electrophoresis device below said cover member; and
  a microprocessor operatively connected to said robotic arm for operating said robotic arm and said pipette.

34. The apparatus of claim 33, further comprising a first horizontal support extending in a first longitudinal direction of said apparatus, wherein said robotic arm is coupled to said first horizontal support and extends therefrom, and wherein said robotic arm is movable along said first horizontal support in said first longitudinal direction.

35. The apparatus of claim 34, wherein said pipette is movable along said robotic arm in a longitudinal direction with respect to said robotic arm.

36. The apparatus of claim 35, wherein said pipette is mounted for reciprocal movement along a vertical axis in a vertical direction substantially perpendicular to a plane of said cover member.

37. The apparatus of claim 33, further comprising a pair of spared apart parallel guide rails and a stop member positioned at one end of said guide rails, wherein said guide rails and said stop member are coupled to said bottom surface of said cover member, said stop member and guide rails being positioned to align gel tubes of a respective electrophoresis device with said apertures in said cover member.

38. The apparatus of claim 33, wherein each of said apertures in said cover member have a frustoconical top surface for guiding said pipette through said apertures.

39. The apparatus of claim 33, wherein each of said electrophoresis devices includes a tank for containing a first buffer solution, a rack supporting a plurality of gel tubes and being positionable in said tank, said rack having a top surface with a well for containing a second buffer solution, said rack further having a plurality of passages for receiving said gel tubes and positioning a top end of said gel tubes in said well.

40. The apparatus of claim 39, wherein said rack includes a first electrode for contacting said first buffer solution and being connected to a first electrical contact, said rack including a second electrode for contacting said second buffer solution and being connected to a second electrical contact, and wherein said guide assembly includes first and second electrical contacts for contacting said first and second electrical contacts of said rack for supplying electrical current to said electrodes.

41. The assembly of claim 34, comprising a first drive motor operatively connected to said robotic arm for moving said robotic arm along said first horizontal support member.

42. The assembly of claim 41, further comprising a second drive motor operatively connected to said pipette for moving said pipette in a vertical direction with respect to said robotic arm.

43. The assembly of claim 42, further comprising a support rod having a longitudinal axis and a lower end, said support rod being coupled to said robotic arm and being movable in said vertical direction, wherein said pipette is coupled to said lower end of said support rod.

44. The assembly of claim 43, wherein said second drive motor is operatively connected to said support rod for moving said support rod in said vertical direction with respect to said movable arm.

45. The assembly of claim 44, wherein said robotic arm includes a longitudinal track and a carriage movable along said track, said second drive motor and said support rod being coupled to said carriage for movement along said track.

* * * * *

UNITED STATES PATENT AND TRADEMARK OFFICE
CERTIFICATE OF CORRECTION

PATENT NO.    : 6,761,810 B2
DATED         : July 13, 2004
INVENTOR(S)   : McGrath et al.

It is certified that error appears in the above-identified patent and that said Letters Patent is hereby corrected as shown below:

Column 1,
Line 13, the following information should be inserted:
-- This invention was made with United States Government support under cooperative agreement number 70NANB5H1075 awarded by the National Institute of Standards and Technology. The government has certain rights in the invention. --.

Signed and Sealed this

Thirteenth Day of September, 2005

JON W. DUDAS
*Director of the United States Patent and Trademark Office*